(12) United States Patent
Hartlep et al.

(10) Patent No.: US 9,901,413 B2
(45) Date of Patent: Feb. 27, 2018

(54) TARGETED INFUSION OF AGENTS FOR TREATMENT OF ALS

(75) Inventors: Andreas Hartlep, Naring (DE); Christoph Pedain, Munich (DE)

(73) Assignee: Brainlab AG, Munich (DE)

(*) Notice: Subject to any disclaimer, the term of this patent is extended or adjusted under 35 U.S.C. 154(b) by 1817 days.

(21) Appl. No.: 11/251,548

(22) Filed: Oct. 14, 2005

(65) Prior Publication Data

US 2006/0094953 A1 May 4, 2006

Related U.S. Application Data

(60) Provisional application No. 60/619,119, filed on Oct. 15, 2004.

(51) Int. Cl.

| A61B 90/00 | (2016.01) |
|---|---|
| A61B 34/20 | (2016.01) |
| A61B 5/0478 | (2006.01) |
| A61B 5/055 | (2006.01) |
| A61B 5/00 | (2006.01) |
| A61B 17/00 | (2006.01) |
| A61B 34/10 | (2016.01) |

(52) U.S. Cl.
CPC .............. *A61B 90/36* (2016.02); *A61B 34/20* (2016.02); *A61B 5/0478* (2013.01); *A61B 5/055* (2013.01); *A61B 5/4839* (2013.01); *A61B 34/10* (2016.02); *A61B 2017/00039* (2013.01); *A61B 2034/2055* (2016.02)

(58) Field of Classification Search
None
See application file for complete search history.

(56) References Cited

U.S. PATENT DOCUMENTS

| 5,205,289 A | 4/1993 | Hardy et al. |
|---|---|---|
| 5,583,902 A | 12/1996 | Bae |
| 5,720,720 A | 2/1998 | Laske et al. |
| 5,735,814 A * | 4/1998 | Elsberry et al. ................ 604/43 |

(Continued)

FOREIGN PATENT DOCUMENTS

| EP | 0 702 966 | 3/1996 |
|---|---|---|
| WO | 01 85230 | 11/2001 |

OTHER PUBLICATIONS

Ochs et al. Amyotrophic Lateral Sclerosis and Other Motor Neuron Disorders, 1(3): 201-206, Jun. 2000.*

(Continued)

*Primary Examiner* — Larry D Riggs, II
(74) *Attorney, Agent, or Firm* — Tucker Ellis LLP

(57) ABSTRACT

A system and method for treating Amyotrophic Lateral Sclerosis (ALS) by delivery of an agent within the brain. At least one image of a target region is acquired, and at least one magnetic resonance diffusion tensor imaging (MR-DTI) scan of the target region is acquired. A diffusion tensor is calculated from the at least one MR-DTI scan, and at least one of an agent distribution and an agent concentration from the images and the calculated diffusion tensor is calculated. Using at least one of the calculated diffusion tensor, the images, the calculated agent distribution, and the calculated agent concentration, the placement of a delivery instrument is planned to deliver the agent to the target region to achieve a desired agent concentration and/or agent distribution within the target region.

21 Claims, 3 Drawing Sheets

(56) References Cited

U.S. PATENT DOCUMENTS

| | | |
|---|---|---|
| 5,919,135 A | 7/1999 | Lemelson |
| 6,026,316 A | 2/2000 | Kucharczyk et al. |
| 6,061,587 A | 5/2000 | Kucharczyk et al. |
| 6,293,282 B1 | 9/2001 | Lemelson |
| 6,464,662 B1 | 10/2002 | Raghavan et al. |
| 6,549,803 B1* | 4/2003 | Raghavan et al. ............ 600/431 |
| 6,572,579 B1 | 6/2003 | Raghavan et al. |
| 7,195,761 B2 | 3/2007 | Holtzman et al. |
| 7,266,227 B2 | 9/2007 | Pedain et al. |
| 2002/0168618 A1 | 11/2002 | Anderson et al. |
| 2003/0028090 A1 | 2/2003 | Raghavan et al. |
| 2004/0006259 A1 | 1/2004 | Pedain et al. |
| 2004/0043418 A1 | 3/2004 | Holtzman et al. |
| 2004/0138551 A1 | 7/2004 | Hartlep et al. |
| 2004/0215143 A1 | 10/2004 | Brady et al. |
| 2004/0236554 A1 | 11/2004 | Raghavan et al. |
| 2005/0186544 A1 | 8/2005 | Raghavan et al. |

OTHER PUBLICATIONS

Esposito et al., Neurobiology of Aging, 23:719-735, 2002.*
Nair et al., NeuroImage, 53:576-583, 2010.*
Azzouz et al., Nature, 429:413-417, 2004.*
U.S. Appl. No. 11/115,093, filed Apr. 2005, Rainer Biskenbach et al.
Iacono et al., "Electrophysiologic Target Localization in Posteroventral Pallidotomy", Movement Disorders and Clinical Neuroscience, 1997, pp. 433-441.
Lopez-Flores, M.D. et al., "Anatomic and Neurophysiological Methods for the Targeting and Lesioning of the Subthalamic Nucleus: Cuban Experience and Review", Neurosurgery, vol. 52, No. 4, Apr. 2003, pp. 817-823.
Chauhan et al., "Effect of Age on the Duration and Extent of Amyloid Plaque Reduction and Microglial Activation After Injection of Anti-Aβ Antibody Into the Third Ventricle of TgCRND8 Mice", Journal of Neuroscience Research vol. 78, 2004, pp. 732-741.
Das et al., "Amyloid-β Immunization Effectively Reduces Amyloid Deposition in FcRγ$^{-/-}$ Knock-Out Mice", The Journal of Neuroscience, vol. 23(24), pp. 8532-8538, (2003).
Solomon et al., "Monoclonal antibodies inhibit in vitro fibrillar aggregation of the Alzheimer β-amyloid peptide", Proc. Natl. Acad. Sci. USA, vol. 93, Jan. 1996, pp. 452-455.
Alterman et al., "Microelectrode Recording during Posteroventral Pallidotomy: Impact on Target Selection and Complications", Neurosurgery, vol. 44, No. 2, Feb. 1999, pp. 315-321.
Angenstein et al., "Age-dependent changes in MRI of motor brain stem nuclei in a mouse model of ALS", Clinical Neuroscience and Neuropathology, vol. 15, No. 14, Oct. 2004, pp. 2271-2274.
György Buzsáki, "Large-scale recording of neuronal ensembles", Nature Neuroscience, vol. 7, No. 5, May 2004, pp. 446-451.
Engelhardt et al., "Antibodies to Calcium Channels From ALS Patients Passively Transferred to Mice Selectively Increase Intracellular Calcium and Induce Ultrastructural Changes in Motoneurons", SYNAPSE 20, 1995, pp. 185-199.
Engelhardt et al., "Subcellular localization of IgG from the sera of ALS patients in the nervous system", Acta Neurol Scand 2005, pp. 126-133.
Esposito et al., "A review of specific dietary antioxidants and the effects on biochemical mechanisms related to neurodegenerative processes", Neurobiology of Aging, 23, 2002, pp. 719-735.
Krause et al., "Deep brain stimulation for the treatment of Parkinson's disease: subthalamic nucleus versus globus pallidus internus", J. Neurol Psychiatry, 2001, pp. 464-470.
Hashimoto et al., "Brain-Stem Auditory-Evoked Potentials Recorded Directly From Human Brain-Stem and Thalamus", Brain 1981, pp. 841-859.
Jin et al., "Increased hippocampal neurogenesis in Alzheimer's disease", PNAS, Jan. 2004, vol. 101, No. 1, pp. 343-347.
Kalra et al., "Neuroimaging in amyotrophic lateral sclerosis", ALS and other motor neuron disorders, 2003, vol. 4, pp. 243-248.
Jonsson et al., "Minute quantities of misfolded mutant superoxide dismutase-1 cause amyotrophic lateral sclerosis", Advanced Access publication, Oct. 2003, pp. 73-88.
Kantarci, M.D. et al., "Neuroimaging in Alzheimer disease: an evidence-based review", Neuroimaging Clinics of North America, vol. 13, 2003, pp. 197-209.
López-Villegas et al., "High Spatial Resolution MRI and Proton MRS of Human Frontal Cortex", NMR in Biomedicine, vol. 9, 1996, pp. 297-304.
Lozano, M.D., et al., "Methods for microelectrode-guided posteroventral pallidotomy", J. Neurosurg., vol. 84, Feb. 1996, pp. 194-202.
Mizutani et al., "Amyotrophic Lateral Sclerosis with IgM Antibody against Gangliosides GM2 and GD2", Internal Medicine, vol. 42, No. 3, Mar. 2003, pp. 277-280.
Nair et al., "Diffusion tensor imaging reveals regional differences in the cervical spinal cord in amyotrophic lateral sclerosis", NeuroImage, vol. 53, 2010, pp. 576-583.
Nutt et al., "Randomized, double-blind trial of glial cell line-derived neurotrophic factor (GDNF) in PD", Neurology, vol. 60, 2003, pp. 69-73.
Nuwer et al., "Topographic Mapping of Somatosensory Evoked Potentials Helps Identify Motor Cortex More Quickly in the Operating Room", Brain Topography, vol. 5, No. 1, 1992, pp. 53-58.
Ochs et al., "A phase I/II trial of recombinant methionyl human brain derived nerotrophic factor administered by intrathecal infusion to patients with amyotrophic lateral sclerosis", ALS and other motor neuron disorders, vol. 1, 2000, pp. 201-206.
Papavassiliou, M.D., et al., "Thalamic Deep Brain Stimulation for Essential Tremor: Relation of Lead Location to Outcome", Clinical Studies, vol. 54, No. 5, 2004, pp. 1120-1130.
Wang et al., "Changes in hippocampal volume and shape across time distinguish dementia of the Alzheimer type from healthy aging", NeuroImage, vol. 20, 2003, pp. 667-682.
Waisbren et al., "Treatment of Amyotrophic Lateral Sclerosis and Multiple Sclerosis With Antibiotics", Treating MS and ALS with Antibiotics, pp. 1-10.
Amyotrophic lateral sclerosis from Wikepedia.
Electroenchephalography from Wikepedia, pp. 1-14.
Deep Brain Stimulation for Movement Disorders, Microelectrode Recording (MER), http://www.neuro-jhmi.edu/dbs/mer.htm.
How the Brain and Nerve Cells Change During Alzheimer's Disease, http://www.ahaf.org/alzheimers/about/understanding/brain-nerve-cells.html.
Kanthasamy et al., "Effect of Riluzole on the Neurological and Neuropathological Changes in an Animal Model of Cardiac Arrest-Induced Movement Disorder", The Journal of Pharmacology and Experimental Therapeutics, vol. 288, No. 3, 1999, pp. 1340-1348.
Niebroj-Dobosz I et al., "Effect of Riluzole on serum amino acids in patients with amyotrophic lateral sclerosis", *Acta Neural Scand*, 2002, pp. 39-43.
Application of Pixe in Medical Study: Environmental Minerals and Neurodegenerative Disorders, International Journal of Pixe (IJPIXE), vol. 9, Issues 3-4, 1999, pp. 245-257 (Abstract).

* cited by examiner

TARGETED INFUSION OF AGENTS FOR TREATMENT OF ALS

RELATED APPLICATION DATA

This application claims priority of U.S. Provisional Application No. 60/619,119 filed on Oct. 15, 2004, which is incorporated herein by reference in its entirety.

FIELD OF THE INVENTION

The present invention relates generally to treating Amyotrophic Lateral Sclerosis (ALS) and, more particularly, to treating ALS using a planned targeted delivery of therapeutic substances within the brain and a planned placement of catheters within the brain.

BACKGROUND OF THE INVENTION

Amyotrophic Lateral Sclerosis is a progressive neurodegenerative disease that attacks nerve cells in the brain and the spinal cord, and ultimately is fatal. Motor neurons reach from the brain to the spinal cord and from the spinal cord to the muscles throughout the body. As the motor neurons degenerate, they can no longer send impulses to the muscle fibers that provide muscle movement. The progressive degeneration of the motor neurons in ALS eventually leads to their death. When the motor neurons die, the ability of the brain to initiate and control muscle movement is lost. With all voluntary muscle action affected, patients in the later stages of the disease become totally paralyzed. However, for the vast majority of people their minds remain unaffected.

Early symptoms of ALS often include increasing muscle weakness, especially involving muscles in the arms and legs, and in muscles related to speech, swallowing and breathing. When the muscles no longer receive messages from the motor neurons, the muscles begin to atrophy (waste away).

There are several approaches to treating ALS and its symptoms. However, the only FDA approved medication is Riluzol (Rilutek), which is administered systemic. Riluzol is neuro-protective and inhibits the pre-synaptic release of glutamate, the most important neurotransmitter, and influences the activation of sodium channels. However, systemic administration of neurotropic growth factors is limited due to side effects and to the limited control to gain a specific concentration of effective agents in the target region. Other treatments for ALS involve neurotrophic growth factors or combination therapies with agents from different families of neurotrophic growth factors and/or Riluzol and/or anti-oxidants (e.g., vitamin E).

Recent studies imply the importance of influencing the local concentration of neurotropic growth factors in the central nervous system. Therefore, the agents can be infused directly to target regions or into the cerebrospinal fluid.

Methods of administering a drug or other material to a target part of the body are known in the art. For example, U.S. Pat. No. 6,026,316 discloses a method for targeted drug delivery into a living patient using magnetic resonance (MR) imaging. The method uses MR imaging to track the location of drug delivery and estimate the rate of drug delivery. More particularly, an MR-visible drug delivery device is positioned at a target site to deliver a diagnostic or therapeutic drug solution into the tissue. The spatial distribution kinetics of the injected or infused drug agent are monitored quantitatively and non-invasively using water proton directional diffusion MR imaging to establish the efficacy of drug delivery at a targeted location.

U.S. Pat. No. 5,720,720 discloses a method of high-flow microinfusion that provides convection-enhanced delivery of agents into the brain and other solid tissue structures. The method involves positioning the tip of an infusion catheter within a tissue structure, and supplying an agent through the catheter while maintaining a pressure gradient from the tip of the catheter during infusion. The method can be used to deliver various drugs, protein toxins, antibodies for treatment or imaging, proteins in enzyme replacement therapy, growth factors in the treatment of various neurodegenerative disorders and viruses and gene therapy.

U.S. Pat. No. 5,735,814 discloses techniques for infusing drugs into the brain to treat neurodegenerative disorders by an implantable pump and catheter. The drugs are capable of altering the level of excitation of neurons in the brain. A sensor is used to detect an attribute of the nervous system which reflects the hyperexcitation of the nerve cells projecting onto the degenerating nerve cells, and a microprocessor algorithm analyzes the output from the sensor in order to regulate the amount of drug delivered to the brain.

Finally, U.S. Pat. No. 6,549,803 discloses the movement of material in an organism, such as a drug injected into a brain. The movement is modeled by a uniformly structured field of static constants governing transport by moving fluid and diffusion within the fluid. This supports planning of material introduction, (e.g., infusion, perfusion, retroperfusion, injections, etc.) to achieve a desired distribution of the material, continuing real-time feedback as to whether imaged material is moving as planned and will be distributed as desired, and real-time plan modification to improve results.

SUMMARY OF THE INVENTION

The above discussed prior art discloses techniques for infusing drugs into the brain. The above prior art, however, does not disclose treating ALS using a planned targeted delivery of a therapeutic substance to the brain. The present invention provides such a planned targeted delivery of a therapeutic substance to the brain for the effective treatment of ALS. Additionally, the effectiveness of the plan can be analyzed prior to performing the treatment.

According to one aspect of the invention, there is provided a system and method for treating ALS by delivery of an agent within the brain, wherein a target region of the brain can be identified and a delivery by infusion of the agent to the target region of the brain can be planned.

According to another aspect of the invention, there is provided a system and method for treating ALS, wherein at least one image of a target region and at least one magnetic resonance diffusion tensor imaging (MR-DTI) scan of the target region may be acquired. A diffusion tensor can be calculated from the at least one MR-DTI scan, and at least one of an agent distribution and an agent concentration can be calculated from the images and the calculated diffusion tensor. At least one of the calculated diffusion tensor, the images, the calculated agent distribution, and the calculated agent concentration can be used to plan the placement of a delivery instrument to deliver the agent to the target region to achieve a desired agent concentration and/or agent distribution within the target region.

To the accomplishment of the foregoing and related ends, the invention, then, comprises the features hereinafter fully described and particularly pointed out in the claims. The following description and the annexed drawings set forth in detail certain illustrative embodiments of the invention. These embodiments are indicative, however, of but a few of the various ways in which the principles of the invention may be employed. Other objects, advantages and novel features of the invention will become apparent from the following detailed description of the invention when considered in conjunction with the drawings.

The forgoing and other embodiments of the invention are hereinafter discussed with reference to the drawings.

DETAILED DESCRIPTION

Figure 1:
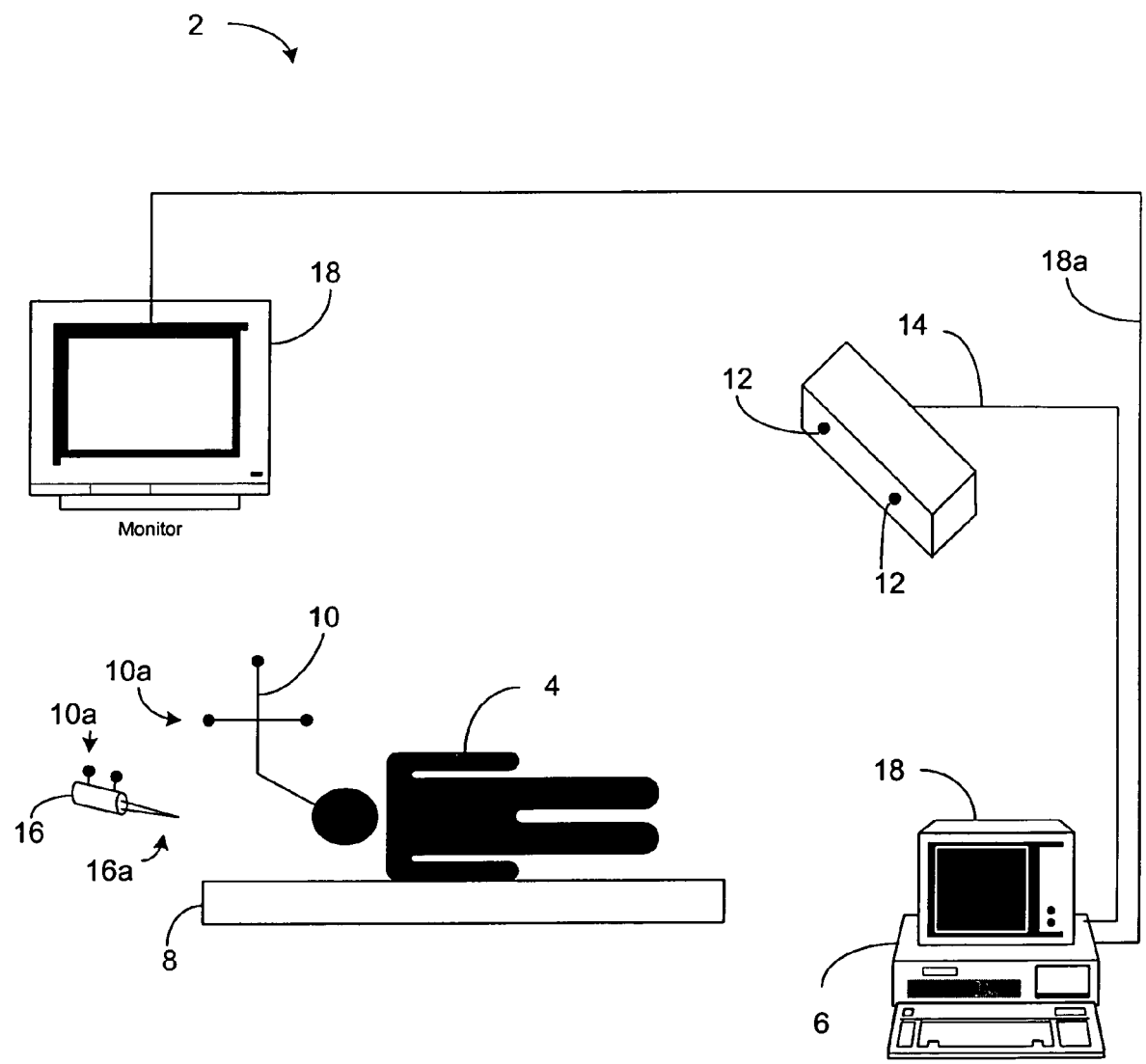
FIG. 1 is a schematic diagram of a navigation system that can be used in conjunction with the present invention.

In general, the term "infusion" is to be understood in accordance with the invention as any administration of a liquid, vapor or solid substance and/or an infusing medium such as medicines, cells, genes, enzymes, proteins, antibodies, hormones, viruses or the like, e.g., viral vectors and viruses such as Adeno-associated virus systems, into body tissue, as opposed to systemic administration of an agent. The substances are introduced directly into body tissue in order to surmount a barrier, such as the blood-brain barrier, for example. The substances can be delivered within a relatively short period of time (e.g., via an injection), or over a longer period of time (e.g., via a continuous and/or variable rate of delivery of the substance). Methods for administering a substance are described in commonly owned U.S. patent application Ser. No. 10/075,108, the entire contents of which is hereby incorporated by reference.

In performing infusion of agents to treat ALS, certain recommended guidelines should be followed. For example, to minimize backflow of the agent along a trajectory of a catheter, the diameter of the catheter lumen should be less than 1.5 millimeters. Alternatively, a specially designed catheter that has varying diameters along its length can be implemented, e.g., a tapered catheter. To keep the backflow less than 3 centimeters, the flow rate of the delivered agent should be less than about 7 micro liters per minute.

A method for targeted infusion of agents in the brain to treat ALS is provided. As used herein, an "agent" or "agents" to be infused includes therapeutic substances such as, for example, neuro-protective substances that inhibit pre-synaptic release of glutamate and/or influence the activation of sodium channels, antioxidants, and any other agent useful for treating ALS through targeted infusion. Riluzol is an example of an agent that can be used in accordance with the present invention.

Patient data and/or patient parameters of the brain are acquired and/or calculated prior to administering the agents. Patient data and/or parameters relating to the brain can be obtained using known techniques, including, for example, magnetic resonance (e.g., dynamic contrast-enhance magnetic resonance imaging, magnetic resonance perfusion imaging) or nuclear spin resonance methods (MRI), computer tomography (CT), positron emission tomography (PET), single photon emission computerized tomography (SPECT), biopsy, x-rays and/or ultrasound. Additionally, other suitable methods that enable the spatial structure of a body and/or a tissue structure (e.g., the brain) to be detected and viewed can be used. In addition to the above imaging techniques, patient parameters such as, for example, tissue density, the distribution of tissue structures, and/or the blood flow through a particular area of tissue, also can be obtained from known data of typical specimens and/or measured using other accepted medical procedures. Such data can be stored in a database, for example.

Once the patient data has been obtained, mathematical models are applied to the data to extract relevant information. Sources (catheters) and sinks (non-intact blood-brain barrier, outflow through sulcii, outflow from cortical surface, binding to cells, etc.) as well as individual anatomy and physiology and catheter positions are considered in modeling the concentration and distribution of the agents. More specifically, data relating to diffusivity, pathways, nerve tracks, conductivity, fluid conductivity, pressure, etc., are extracted from the images and/or other measurements. Using the data, a calculation is made of the possible distribution of the agents and/or the possible concentration of the agents in the target region. In performing the calculations, the extracted information is related to flow (transport mechanisms), efflux (permeability, blood-brain barrier), diffusion (transport mechanisms), conductivity and anatomical (white/grey matter) information. Furthermore, chemical, pharmaceutical and/or biological properties of each agent can be used in the calculations, thereby increasing the specificity of the calculations.

The calculations can be performed, for example, using a computer to execute code that calculates the agent concentration and/or the agent distribution based on known properties of the agent and/or the target region. The computer can provide the results of the calculations via a computer display, for example.

Once the concentration and/or distribution of the agent is determined, the data can be displayed or otherwise reported to medical personnel for evaluation. This can be performed, for example, via a simulation presented on the computer display. More specifically, two-dimensional and/or three-dimensional images of the target region can be viewed on the computer display, along with the expected or calculated concentration and/or distribution of the agent in the target region.

Should the results (e.g., the concentration and/or distribution of the agent) be unsatisfactory, i.e., they do not meet established or otherwise desired criteria for the procedure, then the plan is refined and re-evaluated until a satisfactory plan can be obtained. If, on the other hand, the results are satisfactory, then the plan can be saved and transferred to a navigation system for execution of the plan.

Referring initially to FIG. 1, a medical navigation system 2 that can be used in conjunction with the present invention is illustrated. Navigation systems of various types are well known in the art and therefore will not be discussed in detail herein. Briefly, and by way of example, pre-operative images and/or operative images of a patient 4 are provided to a computer controller 6. The patient 4 is placed on an operating table 8, and a reference star 10 or other suitable trackable device is rigidly fixed to an area of interest of the patient, e.g. the cranium. The reference star 10 can include passive and/or active elements 10a that are detectable by at least two cameras 12 or other detection apparatus. The cameras 12 ascertain the spatial position of the reference star 10 and, therefore, the spatial position of the area of interest, and provide the spatial information to the computer controller 6 via a wired or wireless communications link 14.

Prior to displaying the patient's pre-operative or operative images, the patient 4 is registered into the navigation system 2. Registration is the process of teaching the computer controller 6 the location of the area of interest on the patient with respect to the reference star 10 and correlating the patient location to previously obtained data. This can be done, for example, by indicating to the computer controller 6 the location of several points on the patient 4 using an instrument 16, such as a probe, for example, having active or passive elements 10*a* thereon. Provided the computer controller 6 knows the geometry of the instrument 16, the computer controller can ascertain the location of a tip 16*a* of the instrument. By placing the tip 16*a* of the instrument on several points on the patient 4, the computer controller 6 can ascertain the spatial position of the area of interest with respect to the reference star 10 and correlate the preoperative and/or operative images to the area of interest, thereby completing registration. Once registered, the computer controller 6 displays the images on one or more displays 18 via a video link 18*a*. Those skilled in the art will appreciate that the registration process can be performed in other ways.

As the patient 4 is moved on the table 8, the images displayed on the display 18 also move so as to always show the images with the correct positional relationship. Moreover, one or more instruments 16, such as a catheter, a probe, etc., also can be displayed on the display 18, provided the geometry of each instrument is known by the computer controller 6. A known navigation system is VectorVision™, available from BrainLAB AG, and described, for example, in U.S. Patent Publication No. 2003/0225329, which is hereby incorporated by reference.

Figure 2:
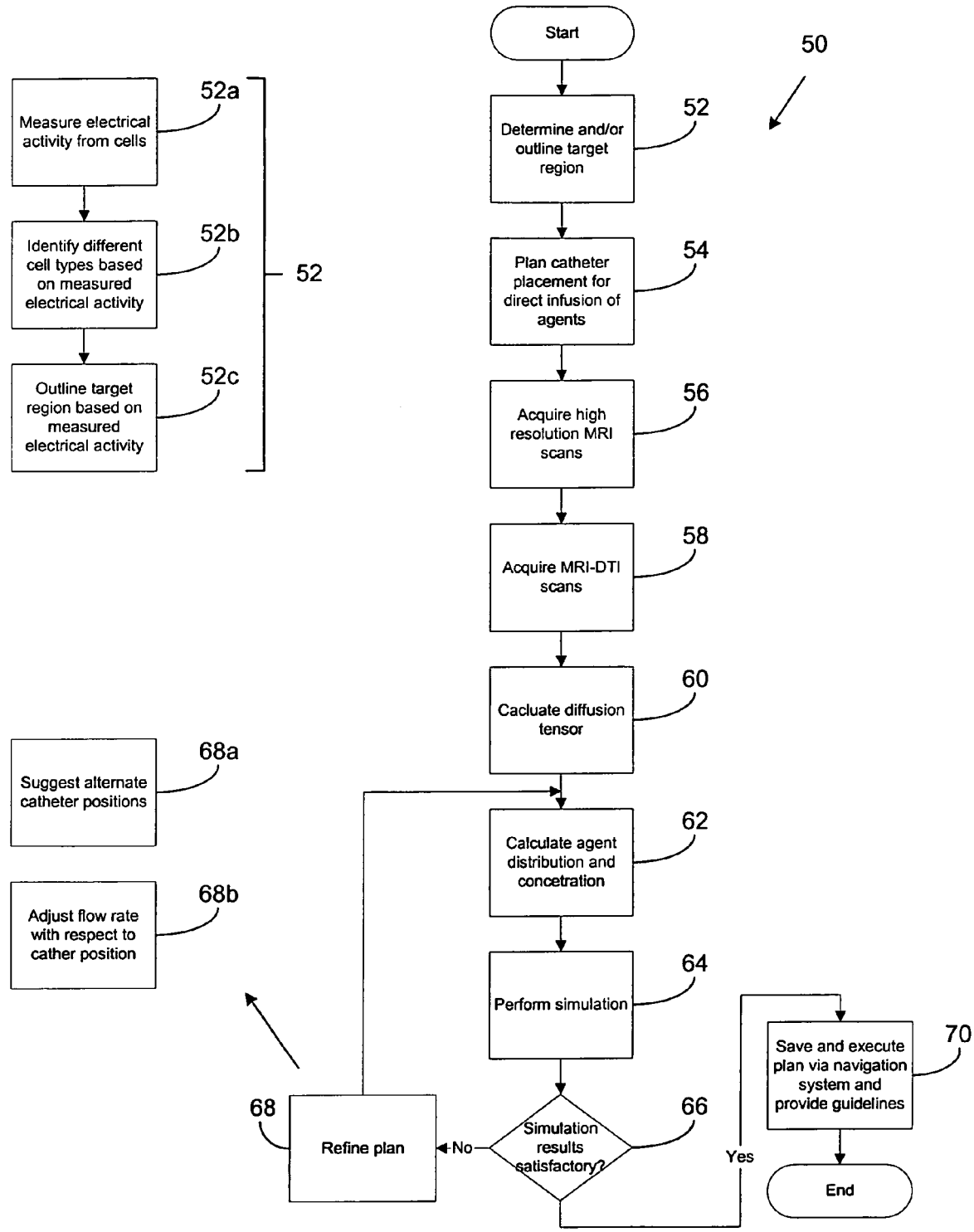
FIG. 2 is a flow diagram for predicting the concentration and/or distribution of an agent in accordance with an embodiment of the invention.

Referring now to FIG. 2, a flow diagram 50 illustrating a method in accordance with an embodiment of the invention is provided. The flow diagram includes a number of process blocks arranged in a particular order. As should be appreciated, many alternatives and equivalents to the illustrated steps may exist and such alternatives and equivalents are intended to fall with the scope of the claims appended hereto. Alternatives may involve carrying out additional steps or actions not specifically recited and/or shown, carrying out steps or actions in a different order from that recited and/or shown, and/or omitting recited and/or shown steps. Alternatives also include carrying out steps or actions concurrently or with partial concurrence.

Beginning at step 52, the target region is determined and/or outlined. For example, it may be known through literature, experience or previous diagnostic tests that a certain region of the brain is responsible for or is affected by ALS, e.g., the hippocampus. Thus, this region can be said to be the target region. If applicable, the target region can be identified by measuring electrical activity from the cells in an area of interest. Cell types having the same amount or type of electrical activity can be classified as the same cell type. The same cell types can be grouped together and classified as the target region, as indicated in alternative steps 52*a*-52*c*.

For example, certain cell types may be known to exhibit a certain amount of electrical activity, while other cell types may exhibit different amounts or different types of electrical activity. As used herein, electrical activity refers to at least one or more of an impedance, a shape of an electrical waveform, an amplitude of the electrical waveform, a frequency of the electrical waveform, or other electrical properties. By monitoring the electrical activity of the cells, different cell types belonging to different tissue regions or abnormal cells can be identified. Based on knowledge obtained from monitoring electrical activity of different cells, a desired target region can be identified and clearly delineated from surrounding cells or regions.

Electrical activity can be monitored by placing measurement electrodes on a catheter or probe and inserting the probe into or near the target region. The measurement electrodes detect the electrical activity and, via a wired or wireless communication link, provide the electrical data to the computer controller 6. The computer controller 6 can analyze the data and establish a pattern for the cell types. Based on a predetermined criteria, e.g., the shape of the waveform, the frequency of the waveform, the amplitude of the waveform, known electrical activity from various regions of the brain, etc., the computer controller 6 can distinguish between different cell types and identify the target region.

Once the target region is determined and/or outlined, with or without the above described procedures, an initial trajectory for a delivery instrument, e.g., a catheter, is planned (catheter planning), as indicated at step 54. The initial trajectory can be based on knowledge and/or experience with a particular procedure, accepted practices by those skilled in the art, recommendations by medical experts and/or medical societies, or any other criteria accepted by those skilled in the art. According to one embodiment, multiple catheters are used to ensure coverage of the entire target area.

Next, at step 56 three-dimensional images of the target region are obtained using any one of several imaging techniques, e.g., MRI, CT, PET, SPECT, etc. The three dimensional images of the target region can be automatically segmented so as to present internal or partial views of the target region as is conventional. For proper identification of the target region (hippocampus), it is preferable to obtain a high resolution MR-T1 image of the target region. According to one embodiment, high resolution MRI scans having at least 1 millimeter in-plane spatial resolutions are obtained of the target region. Additionally, further images can be obtained relating to the anatomy and/or physiology of the patient and/or the target region. The additional images can be obtained using the above mentioned imaging techniques. Such data can be used to identify tissue density and blood flow through a particular area of tissue, for example.

Moving to step 58, MR-DTI scans are acquired of the target region. As is known by those skilled in the art, MR-DTI uses water diffusion to obtain structural information about the brain. MR-DTI can reveal properties of the brain that are not accessible through standard structural MR imaging. Using the MR-DTI scans, the diffusion tensor for the target region is calculated as indicated at step 60.

For example, a 3×3 matrix can represent the diffusion tensor. This may be accomplished with six independent elements. It generally is agreed in the art that at least three directions of the diffusion weighting gradient (which are independent of the preferred directional diffusion) should be sampled to generate trace images. These trace images are the sum of the diagonal elements of the diffusion tensor. Further, a minimum of 6 directions should be sampled for each voxel, if the full diffusion tensor is to be evaluated.

The MR signal of the scan depends on both the direction and magnitude of a diffusion weighting gradient. Through combinations of the x, y, and z gradients, the MR signal can be sensitized to the component of diffusion in any arbitrary direction. The diffusion tensor can be calculated, for example, by obtaining measurements with diffusion weighting gradients in at least six non-collinear directions (since the symmetric tensor itself as six independent components) as well as with no diffusion weighting. In practice, many more directions may be measured, and a fitting procedure can be used to calculate the six tensor components for each voxel.

The distinct structure of the hippocampus requires special imaging parameters for the MR-DTI scans. It is preferable to use a matrix size of $128^2$, and more preferable to use a matrix size of $256^2$. Additionally, the slice thickness of the images should be below 3 millimeters and gaps between slices should be avoided to allow proper three-dimensional reconstruction.

Based on the above acquired data, e.g., MRI, MR-DTI, diffusion tensor, etc., the agent distribution and/or the agent concentration in the target region are calculated as indicated at step 62. More specifically, data relating to diffusivity, pathways, nerve tracks, etc., are extracted from the images and/or measurements. The extracted information then is related to flow (transport mechanisms), efflux (permeability, blood-brain barrier), diffusion (transport mechanisms), conductivity and anatomical (white/grey matter) information to predict possible distribution of the agents and/or possible concentration of the agents in the target region.

For example, and as was noted above, the three dimensional images of the target region can be automatically segmented so as to present internal or partial views of the target region. Anatomical data can be segmented into clusters of similar anatomical and/or physiological properties such as bone, tissue, tissue/vascular system and spinal cord/brain. Next, hydraulic properties and/or vascular or other permeability properties of each cluster can be determined from the obtained anatomical and/or physiological data. Nerve fibers can be tracked by interpreting local variations of diffusivity to determine pathways of nerves in the brain clusters. The determined nerve pathways also can be used to derive the target regions.

In making the above calculations, the blood-brain barrier disruption is assumed to be negligible, so efflux or influx from/to the vascular system of the target region can be neglected. Additionally, perfusion or dynamic T1 data acquisition is not necessary, although they may be applied to determine local variations of vascular permeability, vascular influx or vascular efflux from distinct regions of the target region.

Local variations in pore fraction can be derived from identification and/or segmentation of gray and white matter structures applying known values from the literature. Alternatively, multiple b-value MR-DTI scans can be applied to estimate pore fraction or b0 or T2 images from MRI scans can be used to estimate pore fraction.

Chemical, pharmaceutical and/or biological properties of each agent also can be applied in the above calculations. More specifically, parameters of the agent that characterize the substance to be administered and/or define the physical, chemical and/or biological properties of the agent can be used. The parameters can relate to a molecular or particle size of the substance to be administered, a rate of diffusion of the substance in a particular type of tissue, a metabolism and/or interaction of the substance with tissue due to metabolic processes, a diffusion coefficient known for the substance for the type of tissue to be treated, a preferred injection pressure or pressure gradient, a preferred concentration of the substance, and/or the quantity or rate of delivery. Such data can be stored and retrieved from a database residing on the computer controller 6, for example.

It is noted that should the flow rate of the agent reach zero, then there is no convection, leaving only diffusion as the driver for the distribution process. In such a case, the mathematical model may be adjusted to only use diffusion to calculate agent distribution and concentration (e.g., a model based on the magnetic resonance diffusion tensor imaging (MR-DTI) data and anatomical/physiological data).

Moving to step 64, the acquired data (e.g., the image scans) and the calculated data are combined and used to perform a simulation of the planned infusion. The simulation also can be based on infusion with respect to the individual anatomical environment and/or to chemical and physical properties of the infused agent. Using a simulation, the agent concentration and/or the agent distribution in the target region can be determined statistically and dynamically as a function of time. Thus, it can be established prior to the actual procedure whether the desired agent concentration and agent distribution will be achieved.

For example, and as was noted previously, the images of the target region can be viewed on a computer display and the calculated data, e.g., the expected agent concentration and/or the expected agent distribution, can be included with and/or superimposed on the image scans. By accurately rendering the agent concentration and/or the agent distribution in the target region on the actual images of the target region, medical personnel can visually observe the results of the plan.

Medical personnel, depending on the outcome of the simulation, can determine whether the results are satisfactory or whether further planning is required, as indicated at step 66. Alternatively, the computer controller 6 can provide an indication as to whether the planned infusion meets certain specified criteria and, subject to acceptance by medical personnel, the plan can be implemented. If the plan is acceptable, the plan is saved and executed by the navigation system 2, as indicated at step 70.

According to one embodiment, guidelines are presented to the medical personnel during execution of the plan. For example, the guidelines may present information relating to recommended depths of the catheter or stimulation probe and/or to recommended geometric relations regarding specific anatomical structures.

If the plan is not acceptable, then the plan is refined at step 68 and the process moves back to step 62. The plan can be refined, for example, by changing one or more of the planned depth of the delivery instrument into the target region, the planned entry angle of the delivery instrument, the flow rate of the agent, the amount of agent introduced in the target region, or any other parameter related to delivery of the agent or the agent itself. According to one embodiment, the computer controller 6 presents alternate catheter positions and/or alternate flow rates. The alternate flow rates, for example, can be based on catheter position and/or the specifics of the anatomy and physiology of the target region, as indicated in steps 68a and 68b. The computer controller can be provided with an initial plan and the computer controller 6, using the initial plan, can determine a location and/or delivery of the agent that satisfies a predetermined criteria.

The above described method can be implemented using the computer controller 6 of the navigation system 2 (described in more detail below), or another computer not associated with the navigation system. Additionally, it is noted that the invention can be implemented to be fully automatic, e.g., using data and/or parameters stored in a database, semi-automatic, e.g., selections displayed on a menu are made by an operator, or manual, e.g., values are input by an operator.

Figure 3:
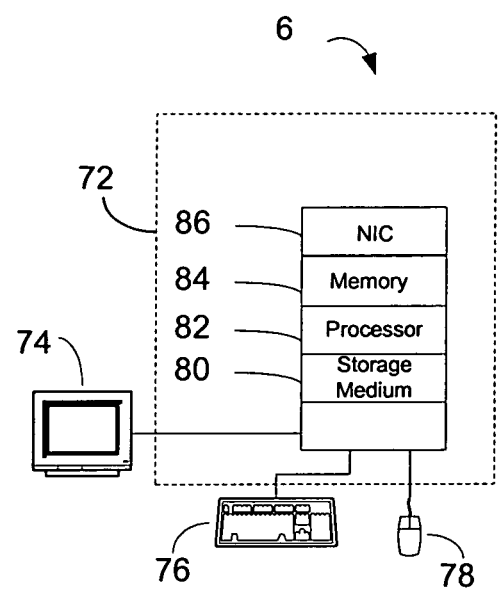
FIG. 3 is a block diagram of a computer system that can be used to implement the method of the present invention.

Moving to FIG. 3, a computer controller 6 for executing a computer program in accordance with the present invention is illustrated. The computer controller 6 includes a computer 72 for processing data, and a display 74 for viewing system information. The technology used in the display is not critical and may be any type currently available, such as a flat panel liquid crystal display (LCD) or a cathode ray tube (CRT) display, or any display subsequently developed. A keyboard 76 and pointing device 78 may be used for data entry, data display, screen navigation, etc. The keyboard 76 and pointing device 78 may be separate from the computer 72 or they may be integral to it. A computer mouse or other device that points to or otherwise identifies a location, action, etc., e.g., by a point and click method or some other method, are examples of a pointing device. Alternatively, a touch screen (not shown) may be used in place of the keyboard 76 and pointing device 78. A touch screen is well known by those skilled in the art and will not be described in detail herein. Briefly, a touch screen implements a thin transparent membrane over the viewing area of the display 74. Touching the viewing area sends a signal to the computer 72 indicative of the location touched on the screen. The computer 72 may equate the signal in a manner equivalent to a pointing device and act accordingly. For example, an object on the display 74 may be designated in software as having a particular function (e.g., view a different screen). Touching the object may have the same effect as directing the pointing device 78 over the object and selecting the object with the pointing device, e.g., by clicking a mouse. Touch screens may be beneficial when the available space for a keyboard 76 and/or a pointing device 78 is limited.

Included in the computer 72 is a storage medium 80 for storing information, such as application data, screen information, programs, etc. The storage medium 80 may be a hard drive, for example. A processor 82, such as an AMD Athlon 64™ processor or an Intel Pentium IV® processor, combined with a memory 84 and the storage medium 80 execute programs to perform various functions, such as data entry, numerical calculations, screen display, system setup, etc. A network interface card (NIC) 86 allows the computer 72 to communicate with devices external to the system 6.

The actual code for performing the functions described herein can be readily programmed by a person having ordinary skill in the art of computer programming in any of a number of conventional programming languages based on the disclosure herein. Consequently, further detail as to the particular code itself has been omitted for sake of brevity.

As will be appreciated, the various computer codes for carrying our the processes herein described can be embodied in computer-readable media. In addition, the various methods and apparatus herein described can be, individually or collectively, supplemented with one or more of the various methods and apparatus described in U.S. patent application Ser. Nos. 10/464,809, 10/661,827, 11/115,093, 10/753,979, 10/771,545, 10/442,989 and 09/745,039, and in U.S. Pat. Nos. 6,464,662, 6,549,803 and 6,572,579, except to which such methods and apparatus are inconsistent with the herein described methods and apparatus. All of the aforesaid patent applications and patents are herein incorporated by reference in their entireties.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A method of operating a navigation system comprising a computer controller including a processor, a non-transient memory device, and a human readable viewable display to develop a treatment plan for treatment of Amyotrophic Lateral Sclerosis (ALS) by delivery of an agent suitable for treating ALS within the brain of an associated patient, the method comprising:

using a device inserted into the brain of the associated patient, identifying a target region of the brain that is to receive the agent, said identifying comprises:
    measuring electrical activity from cells within a region of interest of the brain via the device inserted into the brain;
    identifying different cell types based on the measured electrical activity; and
    identifying the target region to include cell types that exhibit the same electrical activity;

developing an initial plan for delivery of the agent to the target region, the initial plan comprising an initial flow rate of the agent to be introduced into the target region and an initial amount of the agent to be introduced into the target region;

using a magnetic resonance diffusion tensor imaging (MR-DTI) device, imaging the associated patient to obtain anatomical patient data and anatomical patient parameters of the target region, wherein the imaging comprises:
    magnetic resonance diffusion tensor image scanning the target region to obtain MR-DTI data of the associated patient; and
    calculating a diffusion tensor from the MR-DTI data of the associated patient;

performing a computer simulation of a distribution or concentration of the agent in the target region to produce a simulated agent distribution or simulated agent concentration, said simulation based on i) the initial plan for the delivery of the agent to the target region, ii) the anatomical patient data and the anatomical patient parameters, and iii) the calculated diffusion tensor;

outputting the simulation as the treatment plan on the human viewable display for review by rendering the simulation superimposed on the image of the target region; and refining the treatment plan by:
    a) changing the initial plan for the delivery of the agent to the target region to include as a refined initial plan an adjustment of the initial flow rate of the agent to be introduced into the target region or an adjustment of the initial amount of the agent to be introduced into the target region;
    b) performing the computer simulation of the distribution or the concentration of the agent in the target region to produce the simulated agent distribution or the simulated agent concentration, said simulation based on i) the refined initial plan, ii) the anatomical patient data and the anatomical patient parameters, and iii) the calculated diffusion tensor; and c) repeating steps a) and b) until an outcome of the computer simulation of a last-refined treatment plan meets predetermined specified criteria.

2. The method of claim 1, further comprising:
delivering the agent to the target region of the brain based on the last refined treatment plan.

3. The method of claim 2, wherein the agent comprises at least one of an antioxidant or a neurotropic growth factor.

4. The method of claim 2, wherein developing the initial plan comprises developing an initial planned placement of a delivery instrument for delivering the agent, and further comprising adjusting a flow rate of the agent based on an actual placement of the delivery instrument compared to the planned placement of the delivery instrument.

5. The method of claim 1, wherein developing the initial plan comprises planning placement of a delivery instrument for delivering the agent, and further comprising refining the planned placement of the delivery instrument based on the computer simulation of the distribution or the concentration of the agent introduced into the target region.

6. The method of claim 5, further comprising calculating a diffusion tensor of the target region using at least one of chemical, pharmaceutical or biological properties of the agent.

7. The method of claim 1, wherein the agent comprises at least one of an antioxidant or a neurotropic growth factor.

8. The method of claim 1, wherein the imaging the patient to obtain the anatomical patient data and the anatomical patient parameters comprises:
acquiring at least one three-dimensional image of the target region;
wherein the outputting the simulation as the treatment plan on the display comprises rendering the simulation superimposed on the three-dimensional image of the target region.

9. The method of claim 8, wherein the acquiring the at least one three-dimensional image of the target region comprises obtaining image scans that have at least about 1 mm in-plane spatial resolution.

10. The method of claim 1, wherein developing the initial plan comprises developing an initial planned placement of a delivery instrument for delivering the agent, and further comprising providing alternate positions of the delivery instrument to achieve a predetermined agent concentration or distribution in the target region.

11. The method of claim 1, wherein the developing the initial plan comprises developing an initial planned placement of a delivery instrument for delivering the agent, and further comprising providing guidelines for placement of the delivery instrument.

12. The method of claim 2, wherein the delivering the agent to the target region comprises delivering the agent to the target region at a delivery flow rate corresponding to a predetermined flow rate.

13. The method of claim 12, further comprising:
limiting the delivery flow rate to be less than about seven micro-liters per minute.

14. The method of claim 12, further comprising:
limiting the delivery flow rate such that a back flow of the agent is less than about three centimeters from a delivery point of the agent.

15. The method of claim 1, further comprising:
delivering the agent to the target region by diffusion.

16. A method of operating a navigation system comprising a computer controller including a processor, a non-transient memory device, and a human readable viewable display to develop a treatment plan for treatment of Amyotrophic Lateral Sclerosis (ALS) by delivery of an agent suitable for treating ALS within the brain of an associated patient, the method comprising:
using a device inserted into the brain of the associated patient identifying a target region of the brain that is to receive the agent, said identifying comprising:
measuring electrical activity from cells within a region of interest of the brain via the device inserted into the brain;
identifying different cell types based on the measured electrical activity; and
identifying the target region to include cell types that exhibit the same electrical activity;
using an imaging device, scanning the associated patient to acquire at least one image of the target region;
using a magnetic resonance diffusion tensor imaging (MR-DTI) device, MR-DTI imaging the target region to obtain MR-DTI data;
calculating a diffusion tensor from the MR-DTI data;
calculating at least one of an initial agent distribution or an initial agent concentration from the at least one image of the target region and the calculated diffusion tensor;
determining, as the treatment plan, an optimum placement of a delivery instrument to deliver the agent to the target region to achieve a predetermined agent concentration and/or agent distribution within the target region, said determining the optimum placement of the delivery instrument as the treatment plan being based on the calculated diffusion tensor, the at least one image of the target region, the calculated initial agent distribution, and the initial calculated agent concentration, and comprising:
a) determining an initial placement of the delivery instrument, an initial flow rate of the agent, and an initial amount of the agent as an initial treatment plan for the optimum placement of the delivery instrument;
b) changing the initial treatment plan for delivery of the agent to the target region to include as a refined treatment plan an adjustment of the initial flow rate of the agent, an adjustment of the initial amount of agent introduced into the target region or an adjustment of the initial placement of the delivery instrument;
c) performing a computer simulation of the distribution or the concentration of the agent in the target region to produce a simulated agent distribution or a simulated agent concentration, said simulation based on the refined treatment plan and the calculated diffusion tensor; and
d) repeating steps b) and c) until an outcome of the computer simulation meets predetermined specified criteria; and
outputting, on the display, at least one of the agent distribution, the agent concentration or the placement of the delivery instrument superimposed on the at least one image of the target region.

17. The method of claim 16, further comprising
acquiring data relating to individual anatomy and/or physiology of the patient; and
performing a simulation of the agent concentration and/or the agent distribution based on at least one of the anatomy data, the physiology data, the image scans, the MR-DTI scans, the calculated diffusion tensor, the calculated agent concentration or the calculated agent distribution.

18. The method of claim 16, wherein calculating at least one of an agent distribution or an agent concentration comprises simulating at least one of a concentration of the agent in the target region or a distribution of the agent in the target region, and wherein planning the placement comprises refining the planned placement of the delivery instrument based on the simulated agent distribution and/or the simulated agent concentration.

19. A system for treating ALS by delivering an agent within the brain, comprising:
a processor circuit having a processor and a memory;
a treatment sub-system stored in the memory and executable by the processor, the treatment sub-system comprising:
    logic that identifies a target region of the brain that is to receive the agent using a device inserted into the brain of an associated patient, wherein the logic includes:
        logic that measures electrical activity from cells within a region of interest of the brain via the device inserted into the brain;
        logic that identifies different cell types based on the measured electrical activity; and
        logic that identifies the target region to include cell types that exhibit the same electrical activity;
    logic that develops an initial plan for delivery of the agent to the target region of the brain, the initial plan comprising an initial flow rate of the agent to be introduced into the target region and an initial amount of the agent to be introduced into the target region;
    logic that utilizes a magnetic resonance diffusion tensor imaging (MR-DTI) device to image the associated patient to obtain anatomical patient data and anatomical patient parameters of the target region, wherein the logic includes:
        logic that magnetic resonance diffusion tensor image scans the target region to obtain MR-DTI data of the associated patient; and
        logic that calculates a diffusion tensor from the MR-DTI data of the associated patient;
    logic that performs a computer simulation of a distribution or concentration of the agent in the target region to produce a simulated agent distribution or simulated agent concentration, said simulation based on i) the initial plan for the delivery of the agent to the target region, ii) the anatomical patient data and the anatomical patient parameters, and iii) the calculated diffusion tensor;
    logic that outputs the simulation as the treatment plan on the human viewable display for review by rendering the simulation superimposed on the image of the target region; and
    logic that refines the treatment plan by:
        a) changing the initial plan for the delivery of the agent to the target region to include as a refined initial plan an adjustment of the initial flow rate of the agent to be introduced into the target region or an adjustment of the initial amount of the agent to be introduced into the target region;
        b) performing the computer simulation of the distribution or the concentration of the agent in the target region to produce the simulated agent distribution or the simulated agent concentration, said simulation based on i) the refined initial plan, ii) the anatomical patient data and the anatomical patient parameters, and iii) the calculated diffusion tensor; and
        c) repeating steps a) and b) until an outcome of the computer simulation of a last-refined treatment plan meets predetermined specified criteria.

20. The method according to claim 1, wherein the target region of the brain comprises the hippocampus.

21. The method according to claim 20, wherein the agent comprises Riluzole.

* * * * *